United States Patent [19]
Adachi et al.

[11] Patent Number: 5,880,273
[45] Date of Patent: Mar. 9, 1999

[54] PLATELET ACTIVATING FACTOR ACETYLHYDROLASE, AND GENE THEREOF

[75] Inventors: Hideki Adachi; Masafumi Tsujimoto, both of Asaka; Hiroyuki Arai; Keizo Inoue, both of Tokyo, all of Japan

[73] Assignee: Suntory Limited, Osaka, Japan

[21] Appl. No.: 886,152

[22] Filed: Jun. 30, 1997

[30] Foreign Application Priority Data

Jun. 28, 1996 [JP] Japan .................................... 8-188369

[51] Int. Cl.[6] .......................... C07H 21/04; C12N 15/63; C12N 15/00; C12N 1/15
[52] U.S. Cl. ...................... 536/23.2; 435/69.1; 435/71.1; 435/320.1; 435/455; 435/456; 435/459; 435/472; 435/477; 435/250; 435/254.1; 435/183; 530/380; 536/23.5
[58] Field of Search .................... 435/69.1, 250, 435/320.1, 71.1, 254.1, 183, 455, 456, 459, 472, 477; 536/23.5; 530/380

[56] References Cited

FOREIGN PATENT DOCUMENTS 0 638 646 A2  2/1995  European Pat. Off. .

OTHER PUBLICATIONS

Adachi et al. Biochem. Biophys. Res. Communication 214:180, 1996.
Hattori: et al. J. Biol. Chem. 269:23150, 1994.
Mitsuharu Hattori et al, "Purification and Characterization of Bovine Brain Platelet–Activating Factor Acetylhydrolase", The Journal of Biological Chemistry, vol. 268, No. 25, Issue of Sep. 5, pp. 1848–18753, 1993.

Primary Examiner—Thomas M. Cunningham
Assistant Examiner—Martha Lubel
Attorney, Agent, or Firm—Oblon, Spivak, McClelland, Maier & Neustadt, P.C.

[57] ABSTRACT

This invention relates to an isolated and purified DNA encoding an amino acid sequence which comprises SEQ. ID. NO:3.

24 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 392 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
    ( A ) ORGANISM: BOVINE (Bos taurus)

( x i ) SEQUENCE DESCRIPTION: SEQ ID NO:1:

```
Met Gly Val Asn Gln Ser Val Ser Phe Pro Pro Val Thr Gly Pro His
 1               5                  10                  15

Leu Val Gly Cys Gly Asp Val Met Glu Gly Gln Ser Leu Gln Gly Ser
            20                  25                  30

Phe Phe Arg Leu Phe Tyr Pro Cys Gln Glu Ala Glu Thr Ser Glu
        35                  40                  45

Gln Pro Leu Trp Ile Pro Arg Tyr Glu Tyr Cys Ala Gly Leu Ala Glu
    50                  55                  60

Tyr Leu Lys Phe Asn Lys Arg Trp Gly Gly Leu Leu Phe Asn Leu Gly
65                  70                  75                  80

Val Gly Ser Cys Arg Leu Pro Val Ser Trp Asn Gly Pro Phe Lys Thr
                85                  90                  95

Lys Asp Ser Gly Tyr Pro Leu Ile Ile Phe Ser His Gly Met Gly Ala
            100                 105                 110

Phe Arg Thr Val Tyr Ser Ala Phe Cys Met Glu Leu Ala Ser Arg Gly
        115                 120                 125

Phe Val Val Ala Val Pro Glu His Arg Asp Gly Ser Ala Ala Ala Thr
    130                 135                 140

Cys Phe Cys Lys Gln Thr Pro Glu Glu Asn Gln Pro Asp Asn Glu Ala
145                 150                 155                 160

Leu Lys Glu Glu Trp Ile Pro His Arg Gln Ile Glu Glu Gly Glu Lys
                165                 170                 175

Glu Phe Tyr Val Arg Asn Tyr Gln Val His Gln Arg Val Ser Glu Cys
            180                 185                 190

Val Arg Val Leu Lys Ile Leu Gln Glu Val Thr Ala Gly Gln Ala Val
        195                 200                 205

Leu Asn Ile Leu Pro Gly Gly Leu Asp Leu Met Thr Leu Lys Gly Gly
    210                 215                 220

Ile Asp Val Ser Arg Val Ala Val Met Gly His Ser Phe Gly Gly Ala
225                 230                 235                 240

Thr Ala Ile Leu Ala Leu Ala Lys Glu Met Gln Phe Arg Cys Ala Val
                245                 250                 255

Ala Leu Asp Ala Trp Met Phe Pro Leu Glu His Asp Phe Tyr Pro Thr
            260                 265                 270

Ala Arg Gly Pro Ile Phe Phe Ile Asn Ala Glu Lys Phe Gln Thr Val
        275                 280                 285

Glu Thr Val Asn Leu Met Lys Lys Ile Cys Asp Gln His His Gln Ser
    290                 295                 300

Arg Ile Ile Thr Val Leu Gly Ser Val His Arg Ser Leu Thr Asp Phe
305                 310                 315                 320

Val Phe Val Ala Gly Asn Trp Ile Ser Lys Phe Phe Ser Ser His Thr
                325                 330                 335

Arg Gly Ser Leu Asp Pro Tyr Glu Gly Gln Glu Thr Val Val Arg Ala
            340                 345                 350

Met Leu Ala Phe Leu Gln Lys His Leu Asp Leu Lys Glu Asp Tyr Asp
        355                 360                 365

Gln Trp Asn Asn Phe Ile Glu Gly Ile Gly Pro Ser Leu Thr Pro Gly
    370                 375                 380
```

```
            Ala  Pro  His  His  Leu  Ser  Ser  Leu
            385                 390
```

(2) INFORMATION FOR SEQ ID NO:2:

(i) SEQUENCE CHARACTERISTICS:
    (A) LENGTH: 1665 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: BOVINE (Bos taurus)

(ix) FEATURE:
    (A) NAME/KEY: CDS
    (B) LOCATION: 111..1286

(xi) SEQUENCE DESCRIPTION: SEQ ID NO:2:

```
GTCGACCCAC  GCGTCCGAGT  TGACCGTCTG  GGCTGTTTCT  GAGGGTCAAC  GTGACTCGCC        60

GTCAAGTTCA  GCCACTGCCC  AAGTCGTCGT  TCAGTTCAGT  TGGTTATGAG  ATG  GGG         116
                                                           Met  Gly
                                                            1

GTC  AAC  CAG  TCT  GTG  AGC  TTC  CCA  CCC  GTC  ACG  GGA  CCC  CAC  CTC  GTA    164
Val  Asn  Gln  Ser  Val  Ser  Phe  Pro  Pro  Val  Thr  Gly  Pro  His  Leu  Val
               5                   10                       15

GGC  TGT  GGG  GAT  GTG  ATG  GAG  GGT  CAG  AGC  CTC  CAG  GGC  AGC  TTC  TTT    212
Gly  Cys  Gly  Asp  Val  Met  Glu  Gly  Gln  Ser  Leu  Gln  Gly  Ser  Phe  Phe
      20                      25                      30

CGA  CTG  TTC  TAC  CCG  TGC  CAA  GAG  GCA  GAG  GAG  ACC  TCG  GAG  CAG  CCC    260
Arg  Leu  Phe  Tyr  Pro  Cys  Gln  Glu  Ala  Glu  Glu  Thr  Ser  Glu  Gln  Pro
35                       40                      45                       50

CTG  TGG  ATT  CCC  CGC  TAT  GAG  TAC  TGC  GCT  GGC  CTG  GCC  GAA  TAC  CTA    308
Leu  Trp  Ile  Pro  Arg  Tyr  Glu  Tyr  Cys  Ala  Gly  Leu  Ala  Glu  Tyr  Leu
                    55                      60                      65

AAG  TTT  AAT  AAG  CGC  TGG  GGG  GGG  TTA  CTG  TTC  AAC  CTG  GGT  GTG  GGA    356
Lys  Phe  Asn  Lys  Arg  Trp  Gly  Gly  Leu  Leu  Phe  Asn  Leu  Gly  Val  Gly
               70                      75                      80

TCT  TGT  CGC  CTG  CCT  GTT  AGC  TGG  AAT  GGC  CCC  TTT  AAA  ACA  AAG  GAC    404
Ser  Cys  Arg  Leu  Pro  Val  Ser  Trp  Asn  Gly  Pro  Phe  Lys  Thr  Lys  Asp
          85                      90                       95

TCT  GGA  TAC  CCC  TTG  ATC  ATC  TTC  TCT  CAT  GGC  ATG  GGA  GCC  TTC  AGG    452
Ser  Gly  Tyr  Pro  Leu  Ile  Ile  Phe  Ser  His  Gly  Met  Gly  Ala  Phe  Arg
     100                     105                     110

ACA  GTG  TAT  TCA  GCC  TTC  TGC  ATG  GAG  CTG  GCT  TCT  CGT  GGC  TTT  GTG    500
Thr  Val  Tyr  Ser  Ala  Phe  Cys  Met  Glu  Leu  Ala  Ser  Arg  Gly  Phe  Val
115                      120                     125                      130

GTT  GCT  GTA  CCA  GAG  CAC  AGG  GAT  GGG  TCA  GCT  GCG  GCC  ACC  TGT  TTC    548
Val  Ala  Val  Pro  Glu  His  Arg  Asp  Gly  Ser  Ala  Ala  Ala  Thr  Cys  Phe
                    135                     140                     145

TGC  AAG  CAG  ACC  CCA  GAG  GAG  AAC  CAG  CCT  GAC  AAT  GAG  GCC  CTG  AAG    596
Cys  Lys  Gln  Thr  Pro  Glu  Glu  Asn  Gln  Pro  Asp  Asn  Glu  Ala  Leu  Lys
               150                     155                     160

GAG  GAA  TGG  ATC  CCC  CAC  CGT  CAA  ATT  GAG  GAA  GGG  GAG  AAG  GAA  TTC    644
Glu  Glu  Trp  Ile  Pro  His  Arg  Gln  Ile  Glu  Glu  Gly  Glu  Lys  Glu  Phe
          165                     170                     175

TAT  GTT  CGG  AAC  TAC  CAG  GTG  CAT  CAG  AGG  GTG  AGC  GAG  TGT  GTG  AGG    692
Tyr  Val  Arg  Asn  Tyr  Gln  Val  His  Gln  Arg  Val  Ser  Glu  Cys  Val  Arg
     180                     185                     190

GTG  TTG  AAG  ATC  CTA  CAA  GAG  GTC  ACT  GCT  GGG  CAG  GCC  GTT  CTC  AAC    740
Val  Leu  Lys  Ile  Leu  Gln  Glu  Val  Thr  Ala  Gly  Gln  Ala  Val  Leu  Asn
195                      200                     205                      210
```

```
ATC TTG CCT GGC GGA TTG GAT CTG ATG ACC TTG AAG GGC GGC ATT GAC        788
Ile Leu Pro Gly Gly Leu Asp Leu Met Thr Leu Lys Gly Gly Ile Asp
            215                 220                 225

GTG AGC CGT GTG GCT GTA ATG GGA CAT TCA TTT GGA GGG GCC ACA GCT        836
Val Ser Arg Val Ala Val Met Gly His Ser Phe Gly Gly Ala Thr Ala
            230                 235                 240

ATT CTG GCC TTG GCC AAG GAG ATG CAA TTT AGG TGT GCT GTG GCT TTG        884
Ile Leu Ala Leu Ala Lys Glu Met Gln Phe Arg Cys Ala Val Ala Leu
            245                 250                 255

GAC GCT TGG ATG TTT CCT CTG GAG CAT GAC TTT TAC CCC ACG GCC CGA        932
Asp Ala Trp Met Phe Pro Leu Glu His Asp Phe Tyr Pro Thr Ala Arg
            260                 265                 270

GGC CCT ATC TTC TTT ATC AAT GCT GAG AAG TTC CAG ACA GTG GAG ACT        980
Gly Pro Ile Phe Phe Ile Asn Ala Glu Lys Phe Gln Thr Val Glu Thr
275                 280                 285                 290

GTC AAC TTG ATG AAA AAG ATT TGT GAC CAG CAC CAC CAA TCC AGG ATC       1028
Val Asn Leu Met Lys Lys Ile Cys Asp Gln His His Gln Ser Arg Ile
            295                 300                 305

ATA ACT GTC CTT GGT TCT GTT CAT CGG AGT CTA ACC GAC TTT GTT TTT       1076
Ile Thr Val Leu Gly Ser Val His Arg Ser Leu Thr Asp Phe Val Phe
            310                 315                 320

GTG GCT GGT AAC TGG ATT AGT AAA TTC TTC TCC AGT CAC ACC CGT GGA       1124
Val Ala Gly Asn Trp Ile Ser Lys Phe Phe Ser Ser His Thr Arg Gly
            325                 330                 335

AGC TTG GAC CCC TAT GAA GGT CAG GAG ACC GTG GTG CGG GCC ATG TTG       1172
Ser Leu Asp Pro Tyr Glu Gly Gln Glu Thr Val Val Arg Ala Met Leu
            340                 345                 350

GCC TTC CTG CAG AAG CAT CTT GAC CTG AAA GAG GAC TAT GAC CAG TGG       1220
Ala Phe Leu Gln Lys His Leu Asp Leu Lys Glu Asp Tyr Asp Gln Trp
355                 360                 365                 370

AAC AAC TTC ATT GAA GGC ATT GGC CCA TCA CTG ACC CCA GGG GCC CCA       1268
Asn Asn Phe Ile Glu Gly Ile Gly Pro Ser Leu Thr Pro Gly Ala Pro
            375                 380                 385

CAC CAT CTG TCC AGC CTG TAGGCACAAC TGGTCATCTT GTGGAAGGTC              1316
His His Leu Ser Ser Leu
            390

CCTGAGCTGA GTTCCCGTGT GGGGCCTGCC CAGGGATACC CTTGGCCTCC TATCAGGAAG     1376

TGATTGCCAT GACCCTTCTG TGTTGATTGA GAGGATATAA TCACACTGCT GATTGGTAAC     1436

GGGGTACTTG GATTCTCAGA CTTGTCGATC TTAAACTCAT GTTGGGACTT GGGTTCACTT     1496

ACTGATGGGC AAACGGGCAT TCTGAGGACT GAGCCTTAAT GGTATGGAGA ACAAACAGTG     1556

GGATGGGGCT GGGGAAGATC TAAGCCCTAA GCTGGGCACT ATGAGCCCTA TAAACCCAAC     1616

CAGCCAACAC CCTCACCTTG GGCAAGTATG ACTTCTGCAG GTCGACTCT                 1665
```

( 2 ) INFORMATION FOR SEQ ID NO:3:

( i ) SEQUENCE CHARACTERISTICS:
        ( A ) LENGTH: 392 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN ( x i ) SEQUENCE DESCRIPTION: SEQ ID NO:3:

```
Met Gly Val Asn Gln Ser Val Gly Phe Pro Pro Val Thr Gly Pro His
 1               5                  10                  15
```

```
Leu  Val  Gly  Cys  Gly  Asp  Val  Met  Glu  Gly  Gln  Asn  Leu  Gln  Gly  Ser
          20                       25                      30

Phe  Phe  Arg  Leu  Phe  Tyr  Pro  Cys  Gln  Lys  Ala  Glu  Glu  Thr  Met  Glu
               35                       40                 45

Gln  Pro  Leu  Trp  Ile  Pro  Arg  Tyr  Glu  Tyr  Cys  Thr  Gly  Leu  Ala  Glu
     50                       55                      60

Tyr  Leu  Gln  Phe  Asn  Lys  Arg  Cys  Gly  Gly  Leu  Leu  Phe  Asn  Leu  Ala
65                       70                      75                          80

Val  Gly  Ser  Cys  Arg  Leu  Pro  Val  Ser  Trp  Asn  Gly  Pro  Phe  Lys  Thr
               85                       90                           95

Lys  Asp  Ser  Gly  Tyr  Pro  Leu  Ile  Ile  Phe  Ser  His  Gly  Leu  Gly  Ala
               100                 105                      110

Phe  Arg  Thr  Leu  Tyr  Ser  Ala  Phe  Cys  Met  Glu  Leu  Ala  Ser  Arg  Gly
               115                 120                      125

Phe  Val  Val  Ala  Val  Pro  Glu  His  Arg  Asp  Arg  Ser  Ala  Ala  Thr  Thr
          130                 135                      140

Tyr  Phe  Cys  Lys  Gln  Ala  Pro  Glu  Glu  Asn  Gln  Pro  Thr  Asn  Glu  Ser
145                      150                 155                          160

Leu  Gln  Glu  Glu  Trp  Ile  Pro  Phe  Arg  Arg  Val  Glu  Glu  Gly  Glu  Lys
               165                      170                      175

Glu  Phe  His  Val  Arg  Asn  Pro  Gln  Val  His  Gln  Arg  Val  Ser  Glu  Cys
               180                      185                 190

Leu  Arg  Val  Leu  Lys  Ile  Leu  Gln  Glu  Val  Thr  Ala  Gly  Gln  Thr  Val
               195                 200                      205

Phe  Asn  Ile  Leu  Pro  Gly  Gly  Leu  Asp  Leu  Met  Thr  Leu  Lys  Gly  Asn
     210                      215                 220

Ile  Asp  Met  Ser  Arg  Val  Ala  Val  Met  Gly  His  Ser  Phe  Gly  Gly  Ala
225                           230                 235                       240

Thr  Ala  Ile  Leu  Ala  Leu  Ala  Lys  Glu  Thr  Gln  Phe  Arg  Cys  Ala  Val
               245                      250                      255

Ala  Leu  Asp  Ala  Trp  Met  Phe  Pro  Leu  Glu  Arg  Asp  Phe  Tyr  Pro  Lys
               260                 265                      270

Ala  Arg  Gly  Pro  Val  Phe  Phe  Ile  Asn  Thr  Glu  Lys  Phe  Gln  Thr  Met
               275                 280                      285

Glu  Ser  Val  Asn  Leu  Met  Lys  Lys  Ile  Cys  Ala  Gln  His  Glu  Gln  Ser
     290                 295                      300

Arg  Ile  Ile  Thr  Val  Leu  Gly  Ser  Val  His  Arg  Ser  Gln  Thr  Asp  Phe
305                      310                 315                          320

Ala  Phe  Val  Thr  Gly  Asn  Leu  Ile  Gly  Lys  Phe  Phe  Ser  Thr  Glu  Thr
               325                      330                      335

Arg  Gly  Ser  Leu  Asp  Pro  Tyr  Glu  Gly  Gln  Glu  Val  Met  Val  Arg  Ala
               340                      345                 350

Met  Leu  Ala  Phe  Leu  Gln  Lys  His  Leu  Asp  Leu  Lys  Glu  Asp  Tyr  Asn
          355                      360                 365

Gln  Trp  Asn  Asn  Leu  Ile  Glu  Gly  Ile  Gly  Pro  Ser  Leu  Thr  Pro  Gly
     370                      375                 380

Ala  Pro  His  His  Leu  Ser  Ser  Leu
385                 390
```

( 2 ) INFORMATION FOR SEQ ID NO:4:

( i ) SEQUENCE CHARACTERISTICS:
        ( A ) LENGTH: 2559 base pairs
        ( B ) TYPE: nucleic acid
        ( C ) STRANDEDNESS: single
        ( D ) TOPOLOGY: linear (ii) MOLECULE TYPE: cDNA (vi) ORIGINAL SOURCE:
    (A) ORGANISM: HUMAN (ix) FEATURE:
    (A) NAME/KEY: CDS
    (B) LOCATION: 216..1392

(xi) SEQUENCE DESCRIPTION: SEQ ID NO:4:

| | | |
|---|---|---|
| GCAGGTCTCG ACCCACGCGT CCGCGGACGC GTGGGCGAGA AGTGCTTCCA AGCGTCCATT | | 60 |
| TTGAGCCTTG GAAACTACGA CGACCAAAGG GCCACGGGTT CCTGGGTCGT TTCTCATTTC | | 120 |
| CGTCGAGTTA AACGTCTGGG GCTGCTTCTG AGGAATCAGC TTGGCTGGCC AGCAAGTTCA | | 180 |
| GCTCCGGCAA GTCATTTGAT TCACCCGGTG ATGAA ATG GGG GTC AAC CAG TCT | | 233 |
| | Met Gly Val Asn Gln Ser | |
| | 1               5 | |

```
GTG GGC TTT CCA CCT GTC ACA GGA CCC CAC CTC GTA GGC TGT GGG GAT       281
Val Gly Phe Pro Pro Val Thr Gly Pro His Leu Val Gly Cys Gly Asp
         10                  15                  20

GTG ATG GAG GGT CAG AAT CTC CAG GGG AGC TTC TTT CGA CTC TTC TAC       329
Val Met Glu Gly Gln Asn Leu Gln Gly Ser Phe Phe Arg Leu Phe Tyr
     25                  30                  35

CCC TGC CAA AAG GCA GAG GAG ACC ATG GAG CAG CCC CTG TGG ATT CCC       377
Pro Cys Gln Lys Ala Glu Glu Thr Met Glu Gln Pro Leu Trp Ile Pro
 40                  45                  50

CGC TAT GAG TAC TGC ACT GGC CTG GCC GAG TAC CTG CAG TTT AAT AAG       425
Arg Tyr Glu Tyr Cys Thr Gly Leu Ala Glu Tyr Leu Gln Phe Asn Lys
 55                  60                  65                  70

CGC TGC GGG GGC TTG CTG TTC AAC CTG GCG GTG GGA TCT TGT CGC CTG       473
Arg Cys Gly Gly Leu Leu Phe Asn Leu Ala Val Gly Ser Cys Arg Leu
                     75                  80                  85

CCT GTT AGC TGG AAT GGC CCC TTT AAG ACA AAG GAC TCT GGA TAC CCC       521
Pro Val Ser Trp Asn Gly Pro Phe Lys Thr Lys Asp Ser Gly Tyr Pro
             90                  95                 100

TTG ATC ATC TTC TCC CAT GGC CTA GGA GCC TTC AGG ACT TTG TAT TCA       569
Leu Ile Ile Phe Ser His Gly Leu Gly Ala Phe Arg Thr Leu Tyr Ser
         105                 110                 115

GCC TTC TGC ATG GAG CTG GCC TCA CGT GGC TTT GTG GTT GCT GTG CCA       617
Ala Phe Cys Met Glu Leu Ala Ser Arg Gly Phe Val Val Ala Val Pro
     120                 125                 130

GAG CAC AGG GAC CGG TCA GCG GCA ACC ACC TAT TTC TGC AAG CAG GCC       665
Glu His Arg Asp Arg Ser Ala Ala Thr Thr Tyr Phe Cys Lys Gln Ala
135                 140                 145                 150

CCA GAA GAG AAC CAG CCC ACC AAT GAA TCG CTG CAG GAG GAA TGG ATC       713
Pro Glu Glu Asn Gln Pro Thr Asn Glu Ser Leu Gln Glu Glu Trp Ile
                     155                 160                 165

CCT TTC CGT CGA GTT GAG GAA GGG GAG AAG GAA TTT CAT GTT CGG AAT       761
Pro Phe Arg Arg Val Glu Glu Gly Glu Lys Glu Phe His Val Arg Asn
             170                 175                 180

CCC CAG GTG CAT CAG CGG GTA AGC GAG TGT TTA CGG GTG TTG AAG ATC       809
Pro Gln Val His Gln Arg Val Ser Glu Cys Leu Arg Val Leu Lys Ile
         185                 190                 195

CTG CAA GAG GTC ACT GCT GGG CAG ACT GTC TTC AAC ATC TTG CCT GGT       857
Leu Gln Glu Val Thr Ala Gly Gln Thr Val Phe Asn Ile Leu Pro Gly
     200                 205                 210

GGC TTG GAT CTG ATG ACT TTG AAG GGC AAC ATT GAC ATG AGC CGT GTG       905
Gly Leu Asp Leu Met Thr Leu Lys Gly Asn Ile Asp Met Ser Arg Val
215                 220                 225                 230

GCT GTG ATG GGA CAT TCA TTT GGA GGG GCC ACA GCT ATT CTG GCT TTG       953
Ala Val Met Gly His Ser Phe Gly Gly Ala Thr Ala Ile Leu Ala Leu
```

-continued

```
                235                              240                              245
GCC AAG GAG ACC CAA TTT CGG TGT GCG GTG GCT CTG GAT GCT TGG ATG        1001
Ala Lys Glu Thr Gln Phe Arg Cys Ala Val Ala Leu Asp Ala Trp Met
            250                     255                     260

TTT CCT CTG GAA CGT GAC TTT TAC CCC AAG GCC CGA GGA CCT GTG TTC        1049
Phe Pro Leu Glu Arg Asp Phe Tyr Pro Lys Ala Arg Gly Pro Val Phe
        265                     270                     275

TTT ATC AAT ACT GAG AAA TTC CAG ACA ATG GAG AGT GTC AAT TTG ATG        1097
Phe Ile Asn Thr Glu Lys Phe Gln Thr Met Glu Ser Val Asn Leu Met
    280                     285                     290

AAG AAG ATA TGT GCC CAG CAT GAA CAG TCT AGG ATC ATA ACC GTT CTT        1145
Lys Lys Ile Cys Ala Gln His Glu Gln Ser Arg Ile Ile Thr Val Leu
295                     300                     305                 310

GGT TCT GTT CAT CGG AGT CAA ACT GAC TTT GCT TTT GTG ACT GGC AAC        1193
Gly Ser Val His Arg Ser Gln Thr Asp Phe Ala Phe Val Thr Gly Asn
                315                     320                     325

TTG ATT GGT AAA TTC TTC TCC ACT GAA ACC CGT GGG AGC CTG GAC CCC        1241
Leu Ile Gly Lys Phe Phe Ser Thr Glu Thr Arg Gly Ser Leu Asp Pro
            330                     335                     340

TAT GAA GGG CAG GAG GTT ATG GTA CGG GCC ATG TTG GCC TTC CTG CAG        1289
Tyr Glu Gly Gln Glu Val Met Val Arg Ala Met Leu Ala Phe Leu Gln
        345                     350                     355

AAG CAC CTC GAC CTG AAA GAA GAC TAT AAT CAA TGG AAC AAC CTT ATT        1337
Lys His Leu Asp Leu Lys Glu Asp Tyr Asn Gln Trp Asn Asn Leu Ile
    360                     365                     370

GAA GGC ATT GGA CCG TCG CTC ACC CCA GGG GCC CCC CAC CAT CTG TCC        1385
Glu Gly Ile Gly Pro Ser Leu Thr Pro Gly Ala Pro His His Leu Ser
375                     380                     385                 390

AGC CTG T AGGCACAACT GGCCATTTGT AAAGTCACTT CAGCCAAGTT TTCATTTGGG       1442
Ser Leu

AGCTACCCAA GGGCACCCAT GAGCTCCTAT CAAGAAGTGA TCAACGTGAC CCCTTTTCAC      1502

AGATTGAAAG GTGTAATCAC ACTGCTGCTT GGATAACTGG GTACTTTGAT CTTAGATTTG      1562

ATCTTAAAAT CACTTTGGGA CTGGGATCCC TTGCTGATTG ACAAACAGAC TTTCTGGGAC      1622

CTTGATGGAG TGGGAACAA GCAGTAGAGT GGGACTGGGG GAGACCCAGG CCCCGGGCTG       1682

AGCACTGTGA GGCCTGGATG TGAAGACTCA GCCCAGCGAA GCTCATTCCC TTACCCCCGG      1742

CCAGTGCTGC TGCTTCAGTG GAAGAGATGA AGCCAAAGGA CAGAATGAAA ATCCCTACCT      1802

TCAGAGACTC TAGCCCAGCC CAACACCATC TCTTCCTACC TCTCAGCCTT CTCCCTCCCC      1862

AGGGCCACTT GTTGAAGTCT GAGCACTTTA TGTAAATTTC TAGGTGTGAG CCGTGATCAC      1922

ATTTTCTATT TATTTCCAAG TCTTCTCATT GTATGGAACA TAGTACTACT TATACTTACA      1982

GTAGTAAGTT ATACTTGTGA GCCCACAGAG TGGCAGACAG CATGGCTCTC ACAGCACAGG      2042

GAGAAAAACT GAGGTACACA GAGGTACCTC AGAAGCTCTG GATGTCTTTG GGGTTTTGC       2102

TAAGTGTATC TTGATAGGAA ACAACAAAAG CAGGTTGAGA TGGGGAAGAT GACAGAACAA      2162

CAGTGTTAAA TGGCCATTTG CACAGGCCTT TGCCACAACA GAGAAGTAGT TTGGTCAGCT      2222

AAAACTCAGC TGCAGCCTGG ACAGTAGAGC GAGACCCCAT CTTAAAAATA AGAAGGCTG       2282

GGCGTGGTGG CTCATGCCTG TAATCCCAGC ACTTTGGGAG GCCAAGGCAG GCAGATCACT      2342

TAAGGCCAGG AGTTCAAGAC CACCTGGCCA ACATGGTGAA ACCCCGTCTC TACTAAAAAT      2402

ACAAAAAATT AGCCTGGCGT AATGGCAGGC GCCTATAATC CCAGCTACTC AGGAGGCTGA      2462

AGCAGAAGAA TCACTTGAAC CTAGGAGGCG GAGGTTGCAG TGAGTCAAGA TCGCGCCACT      2522

GCACTCCAGC CTGGGTGACA GAGCAAGACT CTGTCTT                               2559
```

PLATELET ACTIVATING FACTOR ACETYLHYDROLASE, AND GENE THEREOF

BACKGROUND OF THE INVENTION a) Field of the Invention

This invention relates to a novel platelet activating factor acetylhydrolase, and a gene encoding the same.

b) Description of the Related Art

A platelet activating factor acetylhydrolase is an enzyme, which acts on a platelet activating factor (hereinafter abbreviated as "PAF") and eliminates its 2-acetyl group to deprive PAF of its activity. Since PAF is a mediator for inflammation which causes defluxion of tissue fluid through finer vessels, vasodilation, smooth muscle contraction, endothelial adhesion, activation of neutrophils, macrophages or eosinophilic leukocytes, or the like, PAF acetylhydrolase is usable as a preventive or therapeutic for various diseases caused by PAF.

Some reports have been made about PAF acetylhydrolase to date. For its use as a medicine, however, there is an outstanding desire for the provision of a PAF acetylhydrolase having higher purity and stronger action compared with conventional PAF acetylhydrolase. Further, from the viewpoint of safety, PAF acetylhydrolase derived form human being instead of an animal is desired.

SUMMARY OF THE INVENTION

With the foregoing in view, the present invention has as a primary object the provision of PAF acetylhydrolase which can fulfill the above-described desires.

Interested in the wide-spread distribution of PAF acetylhydrolase in animal organs such as the brain and kidneys, the present inventors chose the bovine liver as a source, and by various isolation and purification procedures, progressively increased the purity of PAF acetylhydrolase while placing a focus on its enzymatic activity. As a result, the present inventors have succeeded in obtaining bovine PAF acetylhydrolase as a pure product and further in determining its amino acid sequence. In addition, from the amino acid sequence of the PAF acetylhydrolase, a gene encoding the enzyme has been found by methods known per se in the art.

Moreover, using the bovine PAF acetylhydrolase cDNA, the present inventors have also succeeded in identifying the human PAF acetylhydrolase cDNA.

The present invention has been completed based on these findings, and provides a human PAF acetylhydrolase, which plays an important role as a PAF-inhibiting substance, and also a gene which encodes the enzyme and is important for the synthesis of the enzyme by genetic engineering.

The human PAF acetylhydrolase according to the present invention selectively degrades PAF and hence, is usable as medicines or biochemical reagents for the prevention and treatment of diseases caused by PAF, for example, diseases such as asthma, exudative tympanitis, hemorrhagic colitis and adult respiratory distress syndrome.

DETAILED DESCRIPTION OF THE INVENTION AND PREFERRED EMBODIMENTS

The human PAF acetylhydrolase according to the present invention can be prepared as will be described next. PAF acetylhydrolase is first collected from an animal. From the PAF acetylhydrolase, the animal PAF acetylhydrolase cDNA is determined. Using the animal PAF acetylhydrolase cDNA, the human PAF acetylhydrolase cDNA is detected from a human gene library. The human PAF acetylhydrolase cDNA is inserted in an appropriate vector and then cultured in an adequate host organism, whereby the human PAF acetylhydrolase is obtained.

Upon practice of the present invention, it is first necessary to obtain animal PAF acetylhydrolase from an organ of an animal such as the brain, liver or kidneys by purifying it through repetitions of known isolation and purification procedures while using PAF acetylhydrolase activity as an index. A description will hereinafter be made of a process for obtaining PAF acetylhydrolase by using a bovine liver as an example.

As the bovine liver to be used as a source, one obtained from a bovine immediately after its slaughter is preferred.

After the bovine liver is first washed with an appropriate buffer (for example, 10 mM Tris-HCl buffer containing 250 mM sucrose and 1 mM EDTA and having a pH of 7.4), it is homogenized with the same buffer. The homogenate is then centrifuged to obtain a soluble fraction.

Making combined use of hydrophobic chromatography, ion exchange chromatography, adsorption chromatography, gel filtration chromatography and the like, the soluble fraction is purified until a single peak is observed by Mono Q FPLC, so that PAF acetyl hydrolase can be obtained.

Incidentally, PAF acetylhydrolase activity which is used as an index for the selective collection of the PAF-acetylhydrolase-containing fraction can be determined, for example, by the method disclosed in Japanese Patent Application Laid-Open (Kokai) No. HEI 7-39373.

With respect to the bovine PAF acetylhydrolase obtained in the above-described manner, its amino acid sequence was investigated by a method known per se in the art. As a result, the amino acid sequence has been found to be represented by the following formula (III) (SEQ. ID. NO:1):

III

| Met | Gly | Val | Asn | Gln | Ser | Val | Ser | Phe | Pro | Pro | Val | Thr | Gly | Pro |
|-----|-----|-----|-----|-----|-----|-----|-----|-----|-----|-----|-----|-----|-----|-----|
| His | Leu | Val | Gly | Cys | Gly | Asp | Val | Met | Glu | Gly | Gln | Ser | Leu | Gln |
| Gly | Ser | Phe | Phe | Arg | Leu | Phe | Tyr | Pro | Cys | Gln | Glu | Ala | Glu | Glu |
| Thr | Ser | Glu | Gln | Pro | Leu | Trp | Ile | Pro | Arg | Tyr | Glu | Tyr | Cys | Ala |
| Gly | Leu | Ala | Glu | Tyr | Leu | Lys | Phe | Asn | Lys | Arg | Trp | Gly | Gly | Leu |
| Leu | Phe | Asn | Leu | Gly | Val | Gly | Ser | Cys | Arg | Leu | Pro | Val | Ser | Trp |
| Asn | Gly | Pro | Phe | Lys | Thr | Lys | Asp | Ser | Gly | Tyr | Pro | Leu | Ile | Ile |
| Phe | Ser | His | Gly | Met | Gly | Ala | Phe | Arg | Thr | Val | Tyr | Ser | Ala | Phe |
| Cys | Met | Glu | Leu | Ala | Ser | Arg | Gly | Phe | Val | Val | Ala | Val | Pro | Glu |
| His | Arg | Asp | Gly | Ser | Ala | Ala | Ala | Thr | Cys | Phe | Cys | Lys | Gln | Thr |
| Pro | Glu | Glu | Asn | Gln | Pro | Asp | Asn | Glu | Ala | Leu | Lys | Glu | Glu | Trp |

-continued (III)

| | | | | | | | | | | | | | | | |
|---|---|---|---|---|---|---|---|---|---|---|---|---|---|---|---|
| Ile | Pro | His | Arg | Gln | Ile | Glu | Glu | Gly | Glu | Lys | Glu | Phe | Tyr | Val |
| Arg | Asn | Tyr | Gln | Val | His | Gln | Arg | Val | Ser | Glu | Cys | Val | Arg | Val |
| Leu | Lys | Ile | Leu | Gln | Glu | Val | Thr | Ala | Gly | Gln | Ala | Val | Leu | Asn |
| Ile | Leu | Pro | Gly | Gly | Leu | Asp | Leu | Met | Thr | Leu | Lys | Gly | Gly | Ile |
| Asp | Val | Ser | Arg | Val | Ala | Val | Met | Gly | His | Ser | Phe | Gly | Gly | Ala |
| Thr | Ala | Ile | Leu | Ala | Leu | Ala | Lys | Glu | Met | Gln | Phe | Arg | Cys | Ala |
| Val | Ala | Leu | Asp | Ala | Trp | Met | Phe | Pro | Leu | Glu | His | Asp | Phe | Tyr |
| Pro | Thr | Ala | Arg | Gly | Pro | Ile | Phe | Phe | Ile | Asn | Ala | Glu | Lys | Phe |
| Gln | Thr | Val | Glu | Thr | Val | Asn | Leu | Met | Lys | Lys | Ile | Cys | Asp | Gln |
| His | His | Gln | Ser | Arg | Ile | Ile | Thr | Val | Leu | Gly | Ser | Val | His | Arg |
| Ser | Leu | Thr | Asp | Phe | Val | Phe | Val | Ala | Gly | Asn | Trp | Ile | Ser | Lys |
| Phe | Phe | Ser | Ser | His | Thr | Arg | Gly | Ser | Leu | Asp | Pro | Tyr | Glu | Gly |
| Gln | Glu | Thr | Val | Val | Arg | Ala | Met | Leu | Ala | Phe | Leu | Gln | Lys | His |
| Leu | Asp | Leu | Lys | Glu | Asp | Tyr | Asp | Gln | Trp | Asn | Asn | Phe | Ile | Glu |
| Gly | Ile | Gly | Pro | Ser | Leu | Thr | Pro | Gly | Ala | Pro | His | His | Leu | Ser |
| Ser | Leu | | | | | | | | | | | | | |

Further, from the peptide sequence of the bovine PAF acetylhydrolase of the formula (III), a gene encoding the enzyme was determined by a method known *per se* in the art. The gene (hereinafter called the "bovine PAF acetylhydrolase cDNA") has been found to be identified by the following formula (IV) (SEQ. ID. NO:2):

(IV)

```
                                              GTCGACCCACGCGTCCGAGTTGACCGT
CTGGGCTGTTTCTGAGGGTCAACGTGACTCGCCGTCAAGTTCAGCCACTGCCCAAGTCGT
CGTTCAGTTCAGTTGGTTATGAG   ATG GGG GTC AAC CAG TCT GTG AGC TTC
CCA CCC GTC ACG GGA CCC CAC CTC GTA GGC TGT GGG GAT GTG ATG
GAG GGT CAG AGC CTC CAG GGC AGC TTC TTT CGA CTG TTC TAC CCG
TGC CAA GAG GCA GAG GAG ACC TCG GAG CAG CCC CTG TGG ATT CCC
CGC TAT GAG TAC TGC GCT GGC CTG GCC GAA TAC CTA AAG TTT AAT
AAG CGC TGG GGG GGG TTA CTG TTC AAC CTG GGT GTG GGA TCT TGT
CGC CTG CCT GTT AGC TGG AAT GGC CCC TTT AAA ACA AAG GAC TCT
GGA TAC CCC TTG ATC ATC TTC TCT CAT GGC ATG GGA GCC TTC AGG
ACA GTG TAT TCA GCC TTC TGC ATG GAG CTG GCT TCT CGT GGC TTT
GTG GTT GCT GTA CCA GAG CAC AGG GAT GGG TCA GCT GCG GCC ACC
TGT TTC TGC AAG CAG ACC CCA GAG GAG AAC CAG CCT GAC AAT GAG
GCC CTG AAG GAG GAA TGG ATC CCC CAC CGT CAA ATT GAG GAA GGG
GAG AAG GAA TTC TAT GTT CGG AAC TAC CAG GTG CAT CAG AGG GTG
AGC GAG TGT GTG AGG GTG TTG AAG ATC CTA CAA CAG GTC ACT GCT
GGG CAG GCC GTT CTC AAC ATC TTG CCT GGC AGA TTG GAT CTG ATG
ACC TTG AAG GGC GGC ATT GAC GTG AGC CGT GTG GCT GTA ATG GGA
CAT TCA TTT GGA GGG GCC ACA GCT ATT CTG GCC TTG GCC AAG GAG
ATG CAA TTT AGG TGT GCT GTG GCT TTG GAC GCT TGG ATG TTT CCT
CTG GAG CAT GAC TTT TAC CCC ACG GCC CGA GGC CCT ATC TTC TTT
ATC AAT GCT GAG AAG TTC CAG ACA GTG GAG ACT GTC AAC TTG ATG
AAA AAG ATT TGT GAC CAG CAC CAC CAA TCC AGG ATC ATA ACT GTC
CTT GGT TCT GTT CAT CGG AGT CTA ACC GAC TTT GTT TTT GTG GCT
GGT AAC TGG ATT AGT AAA TTC TTC TCC AGT CAC ACC CGT GGA AGC
TTG GAC CCC TAT GAA GGT CAG GAG ACC GTG GTG CGG GCC ATG TTG
GCC TTC CTG CAG AAG CAT CTT GAC CTG AAA GAG GAC TAT GAC CAG
TGG AAC AAC TTC ATT GAA GGC ATT GGC CCA TCA CTG ACC CCA GGG
GCC CCA CAC CAT CTG TCC AGC CTG TAG GCACAACTGGTCATCTTGTGGAAG
GTCCCTGAGCTGAGTTCCCGTGTGGGGCCTGCCCAGGGATACCCTTGGCCTCCTATCAGG
AAGTGATTGCCATGACCCTTCTGTGTTGATTGAGAGGATATAATCACACTGCTGATTGGT
AACGGGGTACTTGGATTCTCAGACTTGTCGATCTTAAACTCATGTTGGGACTTGGGTTCA
CTTACTGATGGGCAAACGGGCATTCTGAGGACTGAGCCTTAATGGTATGGAGAACAAACA
GTGGGATGGGGCTGGGGAAGATCTAAGCCCTAAGCTGGGCACTATGAGCCCTATAAACCC
AACCAGCCAACACCCTCACCTTGGGCAAGTATGACTTCTGCAGGTCGACTCT
```

To obtain human PAF acetylhydrolase from the bovine PAF acetylhydrolase cDNA obtained as described above, the human gene library is screened by a method known per se in the art while using the bovine PAF acetylhydrolase cDNA as a template.

Described specifically, the bovine PAF acetylhydrolase cDNA is labeled, for example, by incorporating fluorescein-12-dUTP through PCR. By the colony hybridization technique that selects each positive colony by ECL (Enhanced Chemiluminescence; Amersham K.K.), colonies containing the human PAF acetylhydrolase cDNA can be obtained.

The human PAF acetylhydrolase cDNA obtained as described above has been found to be identified by the following formula (II) (SEQ. ID. NO:4):

(II)

```
                                  GCAGGTCTCGACCCACGCGTCCGCGGACGCGTGGG
CGAGAAGTGCTTCCAAGCGTCCATTTTGAGCCTTGGAAACTACGACGACCAAAGGGCCAC
GGGTTCCTGGGTCGTTTCTCATTTCCGTCGAGTTAAACGTCTGGGGCTGCTTCTGAGGAA
TCAGCTTGGCTGGCCAGCAAGTTCAGCTCCGGCAAGTCATTTGATTCACCCGGTGATGAA
ATG GGG GTC AAC CAG TCT GTG GGC TTT CCA CCT GTC ACA GGA CCC
CAC CTC GTA GGC TGT GGG GAT GTG ATG GAG GGT CAG AAT CTC CAG
GGG AGC TTC TTT CGA CTC TTC TAC CCC TGC CAA AAG GCA GAG GAG
ACC ATG GAG CAG CCC CTG TGG ATT CCC CGC TAT GAG TAC TGC ACT
GGC CTG GCC GAG TAC CTG CAG TTT AAT AAG CGC TGC GGG GGC TTG
CTG TTC AAC CTG GCG GTG GGA TCT TGT CGC CTG CCT GTT AGC TGG
AAT GGC CCC TTT AAG ACA AAG GAC TCT GGA TAC CCC TTG ATC ATC
TTC TCC CAT GGC CTA GGA GCC TTC AGG ACT TTG TAT TCA GCC TTC
TGC ATG GAG CTG GCC TCA CGT GGC TTT GTG GTT GCT GTG CCA GAG
CAC AGG GAC CGG TCA GCG GCA ACC ACC TAT TTC TGC AAG CAG GCC
CCA GAA GAG AAC CAG CCC ACC AAT GAA TCG CTG CAG GAG GAA TGG
ATC CCT TTC CGT CGA GTT GAG GAA GGG GAG AAG GAA TTT CAT GTT
CGG AAT CCC CAG GTG CAT CAG CGG GTA AGC GAG TGT TTA CGG GTG
TTG AAG ATC CTG CAA GAG GTC ACT GCT GGG CAG ACT GTC TTC AAC
ATC TTG CCT GGT GGC TTG GAT CTG ATG ACT TTG AAG GGC AAC ATT
GAC ATG AGC CGT GTG GCT GTG ATG GGA CAT TCA TTT GGA GGG GCC
ACA GCT ATT CTG GCT TTG GCC AAG GAG ACC CAA TTT CGG TGT GCG
GTG GCT CTG GAT GCT TGG ATG TTT CCT CTG GAA CGT GAC TTT TAC
CCC AAG GCC CGA GGA CCT GTG TTC TTT ATC AAT ACT GAG AAA TTC
CAG ACA ATG GAG AGT GTC AAT TTG ATG AAG AAG ATA TGT GCC CAG
CAT GAA CAG TCT AGG ATC ATA ACC GTT CTT GGT TCT GTT CAT CGG
AGT CAA ACT GAC TTT GCT TTT GTG ACT GGC AAC TTG ATT GGT AAA
TTC TTC TCC ACT GAA ACC CGT GGG AGC CTG GAC CCC TAT GAA GGG
CAG GAG GTT ATG GTA CGG GCC ATG TTG GCC TTC CTG CAG AAG CAC
CTC GAC CTG AAA GAA GAC TAT AAT CAA TGG AAC AAC CTT ATT GAA
GGC ATT GGA CCG TCG CTC ACC CCA GGG GCC CCC CAC CAT CTG TCC
AGC CTG TAG GCACAACTGGCCATTTGTAAAGTCACTTCAGCCAAGTTTTCATTTGGG
AGC-
TAC-
CCAAGGGCACCCATGAGCTCCTATCAAGAAGTGATCAACGTGACCCCTTTTCAC
AGAT-
TGAAAGGTGTAATCACACTGCTGCTTGGATAACTGGGTACTTTGATCTTAGATTTG
ATCT-
TAAAATCACTTTGGGACTGGGATCCCTTGCTGATTGACAAACAGACTTTCTGGGAC
CTTGATGGAGTGGGGAACAAGCAGTAGAGTGGGACTGGGGGAGACCCAGGCCCCGGGCTG
AGCACTGTGAGGCCTGGATGTGAAGACTCAGCCCAGCGAAGCTCATTCCCTTACCCCCGG
CCAGTGCTGCTGCTTCAGTGGAAGAGATGAAGCCAAAGGACAGAATGAAAATCCCTACCT
TCA-
GAGACTCTAGCCCAGCCCAACACCATCTCTTCCTACCTCTCAGCCTTCTCCCTCCCC
AGGGCCACTTGTTGAAGTCTGAGCACTTTATGTAAATTTCTAGGTGTGAGCCGTGATCAC
ATTTTCTATTTATTTCCAAGTCTTCTCATTGTATGGAACATAGTACTACTTATACTTACA
GTAGTAAGTTATACTTGTGAGCCCACAGAGTGGCAGACAGCATGGCTCTCACAGCACAGG
GAGAAAAACTGAGGTACACAGAGGTACCTCAGAAGCTCTGGATGTCTTTGGGGGTTTTGC
TAAGTGTATCTTGATAGGAAACAACAAAAGCAGGTTGAGATGGGGAAGATGACAGAACAA
CAGTGTTAAATGGCCATTTGCACAGGCCTTTGCCACAACAGAGAAGTAGTTTGGTCAGCT
AAAACTCAGCTGCAGCCTGGACAGTAGAGCGAGACCCCATCTTAAAAATAAAGAAGGCTG
GGCGTGGTGGCTCATGCCTGTAATCCCAGCACTTTGGGAGGCCAAGGCAGGCAGATCACT
TAAGGCCAGGAGTTCAAGACCACCTGGCCAACATGGTGAAACCCCGTCTCTACTAAAAAT
ACAAAAAATTAGCCTGGCGTAATGGCAGGCGCCTATAATCCCAGCTACTCAGGAGGCTGA
AGCAGAAGAATCACTTGAACCTAGGAGGCGGAGGTTGCAGTGAGTCAAGATCGCGCCACT
GCACTCCAGCCTGGGTGACAGAGCAAGACTCTGTCTT
```

Following conventional procedures, the human PAF acetylhydrolase cDNA obtained as described above is next introduced in an appropriate vector plasmid, and host cells such as mammal cells are then transformed by a commonly-employed recombinant DNA technique to express the human PAF acetylhydrolase. The expression of the human PAF acetylhydrolase can be confirmed by a western blot technique which makes use of an anti-human PAF acetylhydrolase antibody. The introduction into the plasmid, the establishment of the transformed strain, the culture of the strain and the like can be conducted by the general recombinant DNA technology.

From expression systems known to artisans, a suitable expression system can be selected for use in the present invention. It is possible to improve the efficiency of secretion and the level of expression by adding or improving a signal sequence and/or choosing an appropriate host. Although no particular limitation is imposed on host cells, illustrative examples include cultured cells of bacteria, yeasts, other fungi, human and other animals, and cultured cells of plants. Namely, the polynucleotide according to the present invention is inserted in a suitable expression vector, for example, pUC-PL-cl vector, the expression vector is introduced in adequate host cells, for example, *E. Coli* W3110 or the like, and the host cells are then cultured. The target human PAF acetylhydrolase can thereafter be collected as a protein from the thus-obtained cultured matter (cells or culture medium).

As the host, a procaryote or an eucaryote can be used. Usable examples of the procaryote include bacteria especially *Escherichia coli* and Bacillus bacteria, for example, *B. subtilis*. On the other hand, usable examples of the eucaryote include eucaryotic micro-organisms such as yeasts, for example, Saccharomyces yeasts, especially *S. Servisiae;* insect cells such as armyworm (*Spodoptera Frugiperda*) cells and silkworm (*Bombyx mori*) cells; and animal cells such as human cells, monkey cells and mouse cells, especially monkey cells, for example, COS1 and COS 7.

Usable examples of the expression vector include plasmids, pharges, phargemids, viruses [baculoviruses (for insect cells), vaccinia viruses (for animal cells)]. The promoter in the expression vector is selected depending on the host cells. For examples, lac promoters, trp promoters, trc promoters and the like can be used as promoters for bacteria; and adh 1 promoters, pgk promoters and the like can be used as promoters for yeasts. Further, baculovirus polyhedrin promoters can be mentioned as promoters for insects; and early and late promoters of *Simian virus* 40 (SV40) can be mentioned as promoters for animal cells.

When an enhancer is used, for example, the enhancer of SV40 is inserted either upstream or downstream of the gene.

The transformation of the host by the expression vector can be conducted by a common method known per se in the art. Such methods are disclosed, for example, in "Current Protocols in Molecular Biology", John Wiley & Sons, Inc.

The culture of the transformants can also be conducted by a usual method. The purification of the human PAF acetylhydrolase from the cultured matter can be conducted following procedures commonly employed for the isolation and purification of proteins, for example, by ultrafiltration and/or one or more of various column chromatographic procedures, for example, chromatography making use of "Sepharose".

In the above-described manner, the human PAF acetylhydrolase can be advantageously obtained. The human PAF acetylhydrolase according to the present invention is represented by the following formula (I) (SEQ. ID. NO:3):

same function as the peptide represented by the formula (I) (SEQ. ID. NO:3) despite substitution, deletion, addition or the like of amino acids at parts of their sequences.

The bovine PAF acetylhydrolase represented by the formula (III) (SEQ. ID. NO:1) may be contemplated to be available by gene manipulation in a similar manner as the human PAF acetylhydrolase. As a matter of fact, however, the bovine PAF acetylhydrolase cannot be obtained unless eucaryotic host cells are used.

To obtain the bovine PAF acetylhydrolase by gene manipulation, it is therefore necessary to employ as host cells those derived from an eucaryote and to select and use a vector compatible with the host cells.

An antibody against the human PAF acetylhydrolase or bovine PAF acetylhydrolase (which may hereinafter be collectively called the "PAF acetylhydrolase1") according to the present invention can also be obtained following usual procedures.

Described specifically, the antibody can be obtained by sensitizing an animal such as a rabbit with the PAF acetylhydrolase, separating its serum and, if necessary, purifying an immunoglobulin fraction from the serum. To enhance the sensitizing ability of the enzyme in this case, the enzyme in a form bound on a carrier protein such as bovine serum albumin (BSA) or methyl BSA may be used as an immunogen.

Upon sensitizing an animal, the enzyme can also be used together with Freund's complete adjuvant (FCA) or Freund's incomplete adjuvant (FICA) to increase the production of the antibody. It is desired to conduct the sensitization of the animal twice or more. The frequency of sensitization can be determined while checking the antibody titer of the (I)

| Met | Gly | Val | Asn | Gln | Ser | Val | Gly | Phe | Pro | Pro | Val | Thr | Gly | Pro |
|-----|-----|-----|-----|-----|-----|-----|-----|-----|-----|-----|-----|-----|-----|-----|
| His | Leu | Val | Gly | Cys | Gly | Asp | Val | Met | Glu | Gly | Gln | Asn | Leu | Gln |
| Gly | Ser | Phe | Phe | Arg | Leu | Phe | Tyr | Pro | Cys | Gln | Lys | Ala | Glu | Glu |
| Thr | Met | Glu | Gln | Pro | Leu | Trp | Ile | Pro | Arg | Tyr | Glu | Tyr | Cys | Thr |
| Gly | Leu | Ala | Glu | Tyr | Leu | Gln | Phe | Asn | Lys | Arg | Cys | Gly | Gly | Leu |
| Leu | Phe | Asn | Leu | Ala | Val | Gly | Ser | Cys | Arg | Leu | Pro | Val | Ser | Trp |
| Asn | Gly | Pro | Phe | Lys | Thr | Lys | Asp | Ser | Gly | Tyr | Pro | Leu | Ile | Ile |
| Phe | Ser | His | Gly | Leu | Gly | Ala | Phe | Arg | Thr | Leu | Tyr | Ser | Ala | Phe |
| Cys | Met | Gly | Leu | Ala | Ser | Arg | Gly | Phe | Val | Val | Ala | Val | Pro | Glu |
| His | Arg | Asp | Arg | Ser | Ala | Ala | Thr | Thr | Tyr | Phe | Cys | Lys | Gln | Ala |
| Pro | Glu | Glu | Asn | Gln | Pro | Thr | Asn | Glu | Ser | Leu | Gln | Glu | Glu | Trp |
| Ile | Pro | Phe | Arg | Arg | Val | Glu | Gly | Gly | Glu | Lys | Glu | Phe | His | Val |
| Arg | Asn | Pro | Gln | Val | His | Gln | Arg | Val | Ser | Gln | Cys | Leu | Arg | Val |
| Leu | Lys | Ile | Leu | Gln | Glu | Val | Thr | Ala | Gly | Gln | Thr | Val | Phe | Asn |
| Ile | Leu | Pro | Gly | Gly | Leu | Asp | Leu | Met | Thr | Leu | Lys | Gly | Asn | Ile |
| Asp | Met | Ser | Arg | Val | Ala | Val | Met | Gly | His | Ser | Phe | Gly | Gly | Ala |
| Thr | Ala | Ile | Leu | Ala | Leu | Ala | Lys | Glu | Thr | Gln | Phe | Arg | Cys | Ala |
| Val | Ala | Leu | Asp | Ala | Trp | Met | Phe | Pro | Leu | Glu | Arg | Asp | Phe | Tyr |
| Pro | Lys | Ala | Arg | Gly | Pro | Val | Phe | Phe | Ile | Asn | Thr | Glu | Lys | Phe |
| Gln | Thr | Met | Glu | Ser | Val | Asn | Leu | Met | Lys | Lys | Ile | Cys | Ala | Gln |
| His | Glu | Gln | Ser | Arg | Ile | Ile | Thr | Val | Leu | Gly | Ser | Val | His | Arg |
| Ser | Gln | Thr | Asp | Phe | Ala | Phe | Val | Thr | Gly | Asn | Leu | Ile | Gly | Lys |
| Phe | Phe | Ser | Thr | Glu | Thr | Arg | Gly | Ser | Leu | Asp | Pro | Tyr | Glu | Glu |
| Gln | Glu | Val | Met | Val | Arg | Ala | Met | Leu | Ala | Phe | Leu | Gln | Lys | His |
| Leu | Asp | Leu | Lys | Glu | Asp | Tyr | Asn | Gln | Trp | Asn | Asn | Leu | Ile | Glu |
| Gly | Ile | Gly | Pro | Ser | Leu | Thr | Pro | Gly | Ala | Pro | His | His | Leu | Ser |
| Ser | Leu | | | | | | | | | | | | | |

The human PAF acetylhydrolase selectively degrades PAF and oxidized phospholipids and has physiologically active effects such anti-inflammatory effects.

Needless to say, the human PAF acetylhydrolase according to the present invention is not limited to the peptide of the formula (I) (SEQ. ID. NO:3) but includes peptides having homology therewith, namely, peptides having the serum by test sampling of blood. The whole blood of an immune animal may be used by slaughtering it as needed. As an alternative, an immune animal may be subjected to booster sensitization as many times as needed to maintain a constant antibody titer, and blood samples may be collected in small quantities as needed for immediate use. It is also possible to obtain a monoclonal antibody in a usual manner by sensitizing a mouse with the enzyme and then forming hybridomas from spleen cells and myeloma cells of the sensitized mouse.

The present invention will hereinafter be described in further detail by the following examples and reference examples. It is however to be noted that the present invention are by no means limited by or to these examples.

Referential Example 1

Measurement of PAF Acetylhydrolase Activity (1) Using unlabeled lyso PAF (product of Bachem Feinchemikalien AG), 1-O-[1-$^{14}$C] hexadecyl-lyso PAF (product of New England Nuclear Company; hereinafter called the "labeled lyso PAF") was diluted to 4,000 dpm/nmol.

On the other hand, 1-O-hexadecyl-2-[$^3$H-acetyl]-sn-glycero-3-phosphocholine (hereinafter called "$^3$H-acetyl PAF") was diluted to 3,200 dpm/nmol with the unlabeled lyso PAF.

A standard culture system for the measurement of PAF acetylhydrolase was composed of 50 mM Tris-HCl (pH 7.4), 5 mM EDTA, 5 mM 2-mercaptoethanol (2-ME) and 20 nmol $^3$H-acetyl PAF. The total volume of the sample was 0.25 ml.

(2) Measurement of PAF acetylhydrolase activity was conducted by culturing a test sample in the above described standard culture system at 37° C. for 30 minutes, adding 2.5 ml of chloroform/methanol (4:1 V/V) and 0.25 ml of water to terminate the reaction, and then measuring the radioactivity of a small amount (0.6 ml) of each upper layer to determine the amount of the acetate liberated from the $^3$H-acetyl PAF.

Example 1

Obtainment of Bovine PAF Acetylhydrolase (1) A fresh bovine liver was purchased from a slaughterhouse and was then treated within 3 hours of the slaughter. Treatments were all conducted at 0° to 4° C. The liver was homogenized in a Waring blender subsequent to the addition of a homogenizing buffer [10 mM Tris-HCl (pH 7.4), 250 mM sucrose, 1 mM EDTA] in an amount 5 times as much as the liver. The resulting homogenate was centrifuged for 30 minutes under 100,000×g, followed by the removal of a solid portion. The resultant supernatant was centrifuged further for 1 hour under 100,000×g, whereby a dissolved portion was obtained (supernatant portion)

(2) The supernatant portion obtained through the procedures (1) was adjusted to 1M with NaCl. Subsequent to stirring for 15 minutes, the solution was loaded on a "BUTYL TOYOPEARL 650 M" column which had been equilibrated beforehand with a buffer composed of 50 mM Tris-HCl (pH 7.4), 1 mM EDTA and 1M NaCl. After the column was washed with the same buffer, proteins were eluted with a linear gradient of NaCl (1 to 0M). PAF acetylhydrolase activity was eluted as a single peak in 1 to 0M NaCl fractions.

(3) Active fractions from the "BUTYL TOYOPEARL-"column were loaded on a "Q-Sepharose" column which had been equilibrated with 10 mM Tris-HCl (pH 7.4), 1 mM EDTA and 20% (V/V) glycerol (buffer A). The column was washed with the buffer A. Proteins were eluted with a linear gradient of NaCl (0 to 500 mM) in the buffer A. The activity was observed in a fraction eluted with about 300 mM NaCl.

(4) The active fraction from the "Q-Sepharose" column was concentrated to about 6 ml in an "Amicon ultrafiltration cell" in which "YM-10" membranes were used. The thus-concentrated fraction was loaded on a "Biogel A-1.5 m" gel filtration column which had been equilibrated beforehand with 10 mM Tris-HCl (pH 7.4), 200 mM NaCl, 5 mM 2-ME, 20% (V/V) glycerol and 0.5% (W/V) "CHAPS" (buffer B). The activity was eluted as a single peak in a fraction corresponding to a molecular weight of about 40 kDa.

(5) The active fraction from the "Biogel-A 1.5 m" column was loaded on a hydroxyapatite column which had been equilibrated beforehand with 10 mM Tris-HCl (pH 7.4), 5 mM 2-ME, 20% (V/V) glycerol and 0.5% (W/V) "CHAPS" (buffer C). Proteins were eluted with a linear gradient which ranged from the buffer C alone to a buffer C containing 150 mM $KH_2PO_4$. The activity was observed in a fraction which was eluted with about 50 mM $KH_2PO_4$.

(6) The active fraction from the hydroxyapatite column was dialyzed against the buffer C, and was then loaded on an "FPLC Mono Q HR 5/5" column which had been equilibrated beforehand with the buffer C. Proteins were eluted by a linear gradient of NaCl (0 to 500 mM) in the buffer C. The activity was observed in a fraction which was eluted with 250 mM NaCl, and a protein in the fraction was obtained as purified bovine PAF acetylhydrolase.

The total proteins, total activities, purification degrees (in terms of times) and the like in the individual purification steps described above are tabulated below:

| Step | Total proteins (mg) | Total activity (μmol/min) | Activity per weight (nmon/min/mg) | Degree of purification (times) | Yield (%) |
| --- | --- | --- | --- | --- | --- |
| Cytoplasm | 46000 | 73.5 | 1.6 | 1 | 100 |
| BUTYL TOYOPEAL | 680 | 16.3 | 24 | 15 | 22 |
| Q Sepharose FF | 72.4 | 8.96 | 124 | 78 | 12 |
| Biogel A-1.5 m | 6.93 | 7.38 | 1060 | 670 | 10 |
| Hydroxyapatite | 3.45 | 5.29 | 1530 | 960 | 7.2 |
| Mono Q FPLC | 0.3 | 2.16 | 7200 | 4500 | 2.9 |

Example 2

Determination of Amino Acid Sequence of Bovine PAF Acetylhydrolase (1) About 0.2 mg of the purified PAF acetylhydrolase obtained in Example 1 was reduced with 1 mg of dithiothreitol at room temperature for 2 hours, followed by the S-alkylation with 0.6% (W/V) 4-vinylpyridine at room temperature for 2 hours.

Using a 4.6 mm×250 mm "Vydak 304-1251 $C_4$" column which had been equilibrated beforehand with 20% (V/V) acetonitrile containing 0.1% (V/V) trifluoro-acetic acid, the reaction mixture was subjected to reverse phase high-performance liquid chromatography (HPLC). Proteins were then eluted with a linear gradient of acetonitrile (20 to 85% V/V) which contained 0.1% (V/V) trifluoroacetic acid.

(2) 40 kDa polypeptide, which had been purified by the HPLC, was dialyzed against a lysylendopeptidase digestive buffer [0.5M Tris-HCl (pH 8.5) and 4M urea]. Next, 1 μg of a lysylendopeptidase was added to the sample. After the reaction mixture was incubated for 18 hours at 37° C., the reaction mixture was fractionated by reverse phase HPLC through a 4.6 mm×250 mm "Vydak 304-1251 $C_4$" column while using a linear gradient of acetonitrile (5 to 70% V/V) which contained 0.1% (V/V) trifluoroacetic acid.

(3) The amino acid sequence of a peptide fragment obtained by the reverse phase HPLC was determined by an automated sequencer ("Model 477A", trade name; manufactured by Applied Biosystems, Inc.).

The base sequence of the bovine PAF acetylhydrolase, which was determined from the amino acid sequence of the peptide fragment, was as shown above by the formula (III) (SEQ. ID. NO:1).

Further, from the peptide sequence (III) SEQ. ID. NO:1 of the bovine PAF acetylhydrolase, a gene encoding the enzyme was determined by a method known *per se* in the art. The gene was found to be represented by the formula (IV) SEQ. ID. NO:2).

Example 3

Cloning of Non-active Human PAF Acetylhydrolase cDNA

Using as a template the bovine PAF acetylhydrolase cDNA obtained in Example 2, fluorescein-12-dUTP was incorporated in 500,000 clones of each of a fetal human liver cDNA library (pRc/CMV) and a human brain cDNA library (PCMV SPORTS) by PCR. The clones were then subjected to colony hybridization while detecting the labeling reagent by ECL, whereby cloning was conducted. As a result, a single positive clone was obtained from the human brain library.

A plasmid DNA was prepared and the base sequence was determined. The clone was a full-length clone which contained ATG encoding initiating methionine. Encoding 43 N-terminal amino acids were the same as the corresponding amino acids in the sequence of the bovine PAF acetylhydrolase up to the 40th amino acid, and there was poly A at the 3' end. A more accurate determination of the base sequence was conducted. As a result, the cDNA was found to consist of 2188 bp and to contain an ORF (open reading frame) consisting of 253 amino acids. Compared with the bovine PAF acetylhydrolase hydrolase cDNA, 140 amino acids had been deleted. The segment of the deleted 140 amino acids contains a "catalytic triad" of serine, histidine and aspartic acid, which exhibits catalytic activity. The cDNA is therefore not believed to have PAD acetylhydrolase activity.

Hence, a primer was synthesized at positions flanking the deleted region, and PCR was conducted using the library DNA as a template. From the human brain cDNA, two bands were obtained, one corresponding to the above-described cDNA with the 140 amino acids deleted, and the other to a cDNA having substantially the same length as the bovine PAF acetylhydrolase cDNA. From the foregoing, the human brain library DNA was expected to contain, in addition to the above-obtained cDNA, a human PAF acetylhydrolase cDNA which is actually equipped with PAF acetylhydrolase activity.

Example 4

Cloning of Human PAF Acetylhydrolase cDNA

The human brain cDNA library was diluted to give 2000 clones per well, followed by incubation on 5 96-well plates. Subpools consisting of 10 wells were prepared, and positive pools were determined by PCR (Pool Nos. 10, 20, 28, and 38). With respect to these subpools, PCR was conducted well after well, so that positive pools were confirmed (Pool Nos. 10-5, 20-10, and 38-12).

Concerning these pools, incubation was conducted on plates subsequent to dilution. Using the non-active human PAF acetylhydrolase cDNA as a probe, cloning was attempted by hybridization. Labeling of the DNA was conducted with fluorescein 12-dUTP by PCR, and detection tion was carried out by ECL. Positive colonies were obtained from Pool Nos. 10-5 and 20-10. Plasmid DNAs of these clones were replicated, and their base sequences were then determined. As a result, a human PAF acetylhydrolase cDNA represented by the formula (II) (SEQ. ID. NO:4) was obtained from the clones of Pool Nos. 10-5.

Based on the resultant cDNA, the amino acid sequence of the human PAF acetylhydrolase was determined. It was found to be represented by the formula (I) (SEQ. ID. NO:3). Up to 88%, the sequence was the same as that of the bovine PAF acetylhydrolase (346/392 amino acids). On the other hand, it was 42% identical to that of the plasma human PAF acetylhydrolase (162/392 amino acids).

Further, the above cDNA was incorporated in the pUC-Pl-cl vector, introduced in *E. coli* 3110 and then subjected to expression. A band, which corresponded to a protein having a molecular weight of 42 kDa, was detected by SDS-PAGE.

The protein was investigated for activity. Human PAF acetylhydrolase activity was confirmed.

---

We claim:

1. An isolated and purified DNA encoding an amino acid sequence which comprises SEQ ID. NO:3.

2. The DNA of claim 1, which comprises SEQ. ID. NO:4.

3. The DNA of claim 1, which consists of SEQ. ID. NO:4.

4. An expression vector comprising the DNA of claim 1.

5. The expression vector of claim 4, which is a plasmid, phage, phagemid or a virus.

6. The expression vector of claim 4, which is a plasmid.

7. A host cell transformed with the expression vector of claim 4.

8. The host cell of claim 7, which is a procaryote or a eucaryote.

9. The host cell of claim 7, which is a bacterial cell.

10. The host cell of claim 7, which is a yeast, insect or animal cell.

11. A method of producing a protein comprising the amino acid sequence of SEQ. ID. NO:3, comprising culturing the transformed host cell of claim 7 in a culture medium and isolating said protein.

12. An isolated and purified DNA encoding an amino acid sequence which comprises SEQ ID NO: 1.

13. The DNA of claim 12, which comprises SEQ. ID. NO:2.

14. The DNA of claim 12, which consists of SEQ. ID. NO:2.

15. An expression vector comprising the DNA of claim 12.

16. The expression vector of claim 15, which is a plasmid, phage, phagemid or a virus.

17. The expression vector of claim 16, which is a plasmid.

18. A host cell transformed with the expression vector of claim 15.

19. The host cell of claim 18, which is a procaryote or a eucaryote.

20. The host cell of claim 18, which is a eucaryote.

21. The host cell of claim 18, which is a bacterial cell.

22. The host cell of claim 18, which is a yeast, insect or animal cell.

23. A method of producing a protein comprising the amino acid sequence of SEQ. ID. NO:1, comprising culturing the transformed host cell of claim 18 in a culture medium and isolating said protein.

24. A method of producing a protein comprising the amino acid sequence of SEQ. ID. NO:1, comprising culturing the transformed host cell of claim 20 in a culture medium and isolating said protein.

* * * * *